United States Patent [19]

Strauss et al.

[11] 4,419,585
[45] Dec. 6, 1983

[54] VARIABLE ANGLE SLANT HOLE COLLIMATOR

[75] Inventors: H. William Strauss, Newton Centre; Richard H. Moore, Concord; Nathaniel M. Alpert, Swampscott, all of Mass.

[73] Assignee: Massachusetts General Hospital, Boston, Mass.

[21] Appl. No.: 238,582

[22] Filed: Feb. 26, 1981

[51] Int. Cl.³ ..................... G02B 5/00; G21K 1/00; H01J 1/52
[52] U.S. Cl. ........................... 250/505.1; 378/149
[58] Field of Search ............ 250/503, 505, 508, 509, 250/510, 513, 514; 378/149, 150

[56] References Cited

U.S. PATENT DOCUMENTS

| | | | |
|---|---|---|---|
| 1,874,577 | 8/1932 | Morrison | 250/508 |
| 2,138,555 | 11/1938 | Ötvös | 250/509 |
| 2,336,026 | 12/1943 | Millenaar | 250/508 |
| 3,869,615 | 3/1975 | Hoover et al. | 250/508 |
| 3,934,142 | 1/1976 | Hounsfield | 250/514 |
| 4,315,146 | 2/1982 | Rudin | 250/509 |

*Primary Examiner*—Bruce C. Anderson
*Attorney, Agent, or Firm*—Weingarten, Schurgin, Gagnebin & Hayes

[57] ABSTRACT

A variable angle radiation collimator particularly for use in gamma-photon medical diagnostic systems in a gamma-photon camera system for radiological examination of human subjects. The collimator provides collimation of gamma-photon radiation along a single beam direction which may be varied along two axes to adjust exposure angle or to provide a scanning capability. The collimator is a stack of substantially identical radiation-opaque plates, each of which are apertured with a similar array of openings. The combined effect of the stacked aperture plates is to transmit radiation in a predetermined orientation. The collimated angle of the radiation thus generated is controlled by the coincidence of the array of openings. The stack is retained by a mechanism which permits adjustment of the collimation angle, and the plates are fabricated to provide ease of shear motion during such adjustment. In addition, the tradeoff between the resolution and intensity of radiation transmitted may be easily varied by adjusting stack thickness.

16 Claims, 9 Drawing Figures

VARIABLE ANGLE SLANT HOLE COLLIMATOR

The invention described herein was made in the course of work under a grant or award from the Department of Health and Human Services.

FIELD OF THE INVENTION

This invention relates to radiation collimators and gamma and x-ray photon systems as applied to medical radiology and nuclear medicine and more specifically, collimators and systems which provide a collimated radiation beam easily controlled along two axes.

BACKGROUND OF THE INVENTION

The fields of radiology and nuclear medicine typically involve the exposure of a patient to radiation or the introduction of radiation into the patient metabolism or anatomy which can be imaged for diagnostic purposes. Other activities involve theraputic, localized exposure to controlled levels of radiation which is typically intended to affect selected tissue areas.

One of the components of such a radiological system is a collimator which consists of a series of generally parallel, or occasionally converging or diverging channels in the radiation path, the purpose of which is to filter the radiation passing through so as to select radiation only on a predetermined trajectory and within a selected acceptance angle. For example, it is frequently desired to view the radiation from a radioisotope placed in the blood circulatory system at an angle other than orthogonal to the patient's surface. It is additionally desired to detect this radiation as close to the radiation source as possible. For this purpose a collimator having the collimation channels angled at a predetermined angle is applied between the patient skin surface and the radiation detectors as close to the subject area, such as the patient heart, as possible. Collimators to provide this function are known in the art and typically consist of a plurality of generally parallel radiation transmissive channels surrounded by lead wall material. Such collimators are generally hand fabricated at great expense using a corrugated pattern of lead sheet and are thus set at a fixed angle of view. In addition the lead sheet material is normally quite soft making it easy to distort and thus ruin the collimator of such a design.

Such prior art collimators, in addition to being fixed in their slant angle of view, are also fixed in channel length. Channel length in a radiation collimator determines the compromise between collimator resolution, which increases with the channel length to aperture length ratio versus the collimator sensitivity which is reduced with the reduction in acceptance angle that comes from increasing collimator resolution. Thus, in prior art systems, in order to accommodate a range of resolution and sensitivity criteria it has been necessary to possess a number of the expensive prior art design collimators.

One of the recent advances in radiation medicine, tomography or related techniques, involves the use of scanning and imaging radiation equipment. One of the difficulties with this technique is sampling the subject's radiation distribution from an adequate number of view angles.

SUMMARY OF THE INVENTION

In accordance with the teaching of the present invention a collimator, having the desirable features noted above, is provided as a stack of radiation opaque plates apertured in alignment to provide an array of parallel, diverging or converging, radiation transmissive channels. The plates may be generally planar or curve. When the plates are substantially vertically aligned, the angle of view is perpendicular to the planar receiving surface. As the alignment of the plates is skewed, the angle of view will similarly be skewed.

In addition, the collimator according to the present invention has a suitable mounting mechanism which permits controlled adjustment of the skew of the plates and thus the axis of the collimator acceptance angle, as well as facilitating rotation of the collimator in the radiation path of view.

To facilitate adjustment in collimator skew and thus the orientation of the angle of acceptance, the individual plates are formed of a material that allows them to slide easily relative to each other. This ease of variation in the angle of view makes possible complex collimator motion permitting multiple view angles as noted above. In addition, the construction of the collimator as a stack of plates permits a range of resolution/sensitivity compromises to be achieved by adjusting stack height to achieve different acceptance angles with a single collimator.

BRIEF DESCRIPTION OF THE DRAWING

The foregoing and other aspects of the present invention, as well as the more specific features of the present invention, may be better understood from the following detailed description, when read together with the accompanying drawing in which.

DESCRIPTION OF THE PREFERRED EMBODIMENT

Figure 1:
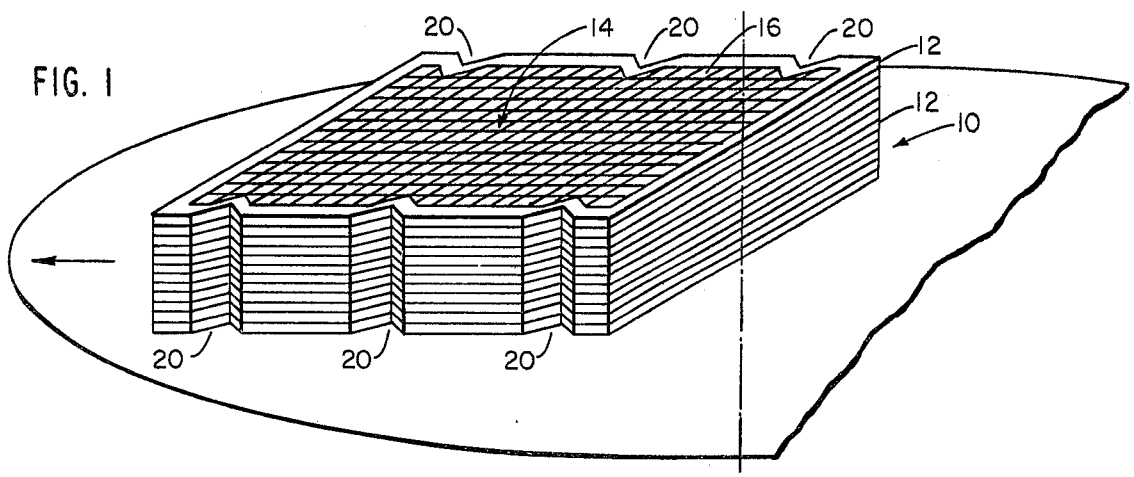
FIG. 1 is a perspective view of the collimator in one embodiment having a plurality of planar plates with apertures in vertical alignment.

The present invention contemplates a radiation collimator comprising a stack of relatively slideable plates formed of a radiation opaque material and apertured in a regular pattern to provide a series of parallel, convergent or divergent radiation transmissive channels therethrough. The collimator of the present invention may best be perceived by reference to FIG. 1 of the drawing showing a stack 10 of individual, radiation opaque sheets 12, the individual sheets 12 being more clearly shown in the cross sectional view of a portion of the stack 10 illustrated in FIG. 1A. Each of the sheets 12 is apertured in a regular pattern 14 of typically square holes 16 to provide for a plurality of, typically, parallel channels 18 through the stack.

Typical dimensions, in the medical radiology field, for the stack 10 would comprise equal widths and depths up to 40 cm×40 cm at a stack height varying with the resolution/sensitivity needs of the application as discussed below. The individual plates 12 have most of their surface area apertured with holes of approximately 2 mm in diameter. A plate thickness, when fabricated of tungsten, of approximately 0.25 mm is typical. While a discussion of plate construction alternatives is provided below with respect to FIG. 7, it should be noted that one of the requirements for plate construction is that the plates be slideable relative to each other with ease in order to permit the adjustment in angle of view as discussed below. A limiting factor in the design of the collimator plate is that each plate accept compression or tension loads due to the shear forces created by plate sliding movement. In the preferred embodiment, tungsten provides an acceptable material in view of its high photo-electric cross-section, mechanical properties of relatively low sliding friction and the applicability of photo-etching techniques for producing the apertures in each of the plates 12. In addition, notches 20 are preferably provided along opposing edges of each of the plates 12 as assembled in the stack 10 in order to facilitate alignment control as the stack is skewed in one direction or another as discussed below.

Figure 1A:
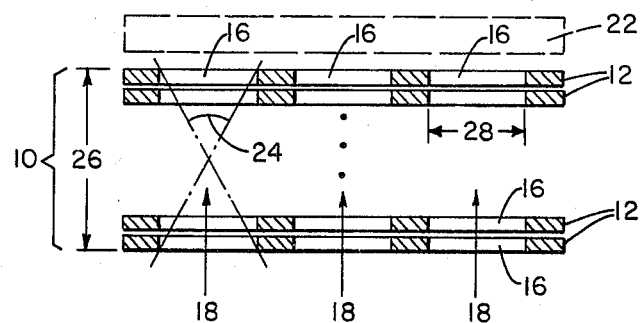
FIG. 1A is a cross sectional view of the collimator of FIG. 1 illustrating the paths of radiation therethrough.

One or more detectors 22, as shown in FIG. 1A, are typically provided at one face of the collimator stack 10 when in use, in order to receive the radiation applied through the collimator and provide an electrical signal representative thereof. One purpose for such a collimator stack 10 is to limit the acceptance angle, represented by the angle 24 in FIG. 1A, so that the field of view of the detectors 22 is limited to a specific area of interest within the body under study. As can be perceived from FIG. 1A, the acceptance angle 24 is a function of the ratio of the stack height 26 to aperture diameter 28. The acceptance angle 24 defines the resolution of the collimator and detector combination with resolution increasing as the angle 24 diminishes. At the same time, because the radiation opaque channel walls of the collimator stack 10 intercept a greater portion of the radiation incident on the collimator as the stack thickness 26 increases, the geometric sensitivity of the collimator will decrease with increased stack thickness.

While normally it would be considered desirable to have both high resolution and high sensitivity, it can be perceived from the view of FIG. 1A that one must be balanced against the other until an acceptable resolution/sensitivity compromise is achieved for the desired application. The collimator of the present invention as represented by FIG. 1A readily accommodates different resolution/sensitivity compromises by the addition or deletion of plates 12 in the collimator stack 10.

Figure 2:
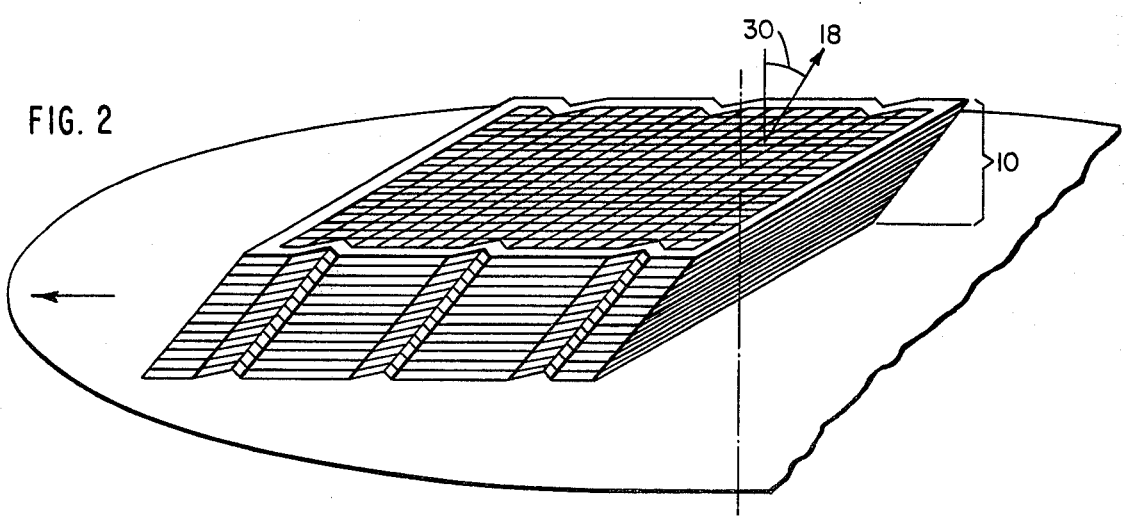
FIG. 2 is a perspective view of the collimator of FIG. 1 having the plates skewed to a non-perpendicular angle of view.
Figure 2A:
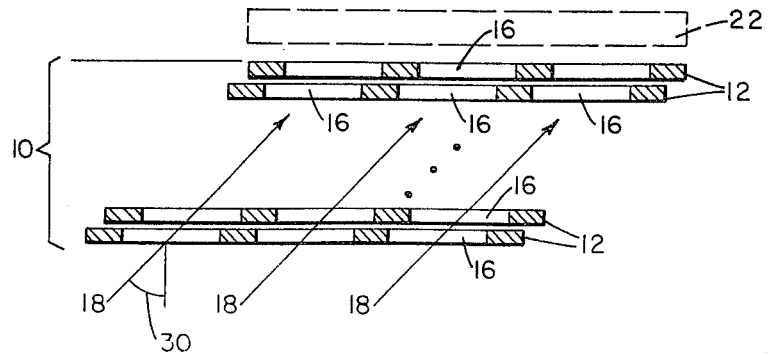
FIG. 2A is a sectional view of the collimator of FIG. 2 showing the paths of collimated radiation transmitted therethrough.

The collimator stack 10 represented in FIGS. 1 and 1A illustrates a field of view substantially perpendicular to the plane of the collimator or the individual sheets 12. One of the features of the present invention is the ability to vary the angle of view from the perpendicular angle represented by the channels 18 to a substantially non-perpendicular angle of view by skewing the stack 10 as illustrated in FIGS. 2 and 2A. In this case, by sliding each of the plates 12 with respect to each other to produce the skewed stack illustrated in FIG. 2 the channel 18 can be angled to the perpendicular by a predetermined angle 30. This is particularly useful where, for example, it is desired to have a view of a functioning, artificially radiating, heart from an angled location on one side of the patient's body. In this case it is desired to place the detector and collimator at an oblique angle of view and as close to the heart as possible. Here, the use of a skewed collimator as illustrated in FIGS. 2 and 2A is particularly useful by permitting it to rest directly on the patient's chest but at a location to the side of the heart cavity while, due to the angled field of view of the collimator, still receiving radiation directly from the heart.

Figure 3:
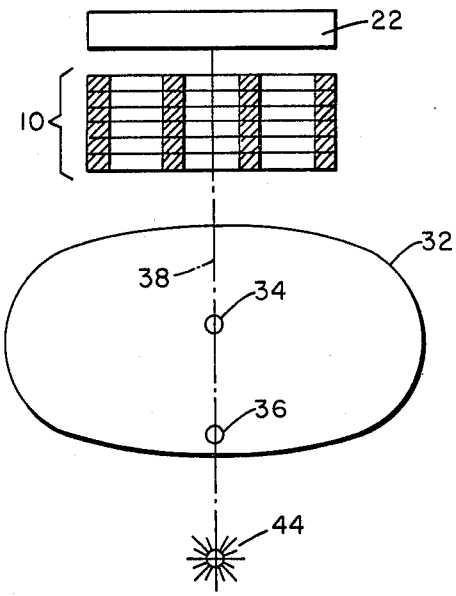
FIG. 3 is a cross sectional view of the collimator of the present invention in the context of a radiology application.
Figure 4:
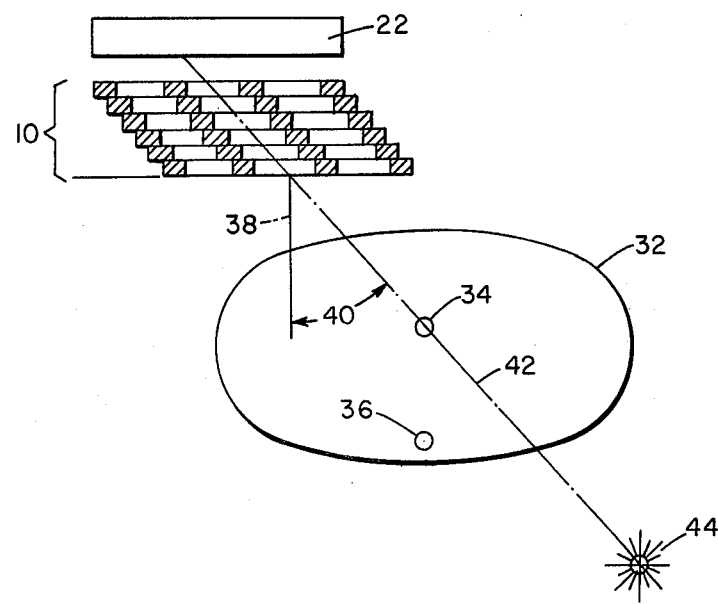
FIG. 4 shows an alteration to the application of FIG. 3.

An advantage of being able to alter the angle of view 30 of the detectors 22, is illustrated in FIGS. 3 and 4, showing the monitoring of a body function without including in the field of view an undesired radiation source. As illustrated in FIG. 3 an object 32 under investigation may have two sources 34 and 36 of radiation which are aligned along the angular view 38 of the collimator stack 10 below the detectors 22. Where it is desired to investigate the source 34, such as a body organ having an artificially induced radiation, it may be impossible in the single view exposure of FIG. 3 to distinguish the activity of organ source 34 from source 36. In this case it may be desirable to provide an additional or alternate exposure at a predetermined slant angle 40 along a different angle of view 42 as illustrated in FIG. 4. This is readily accomplished with the collimator of the present invention by skewing the stack 10 as illustrated.

Additionally, where the object 32 receives radiation from an external source 44 as illustrated in FIG. 3 and FIG. 4, it may be desirable to receive that radiation through the object 32 at a predetermined slant angle such as the slant angle 40 illustrated in FIG. 4.

Figure 5:
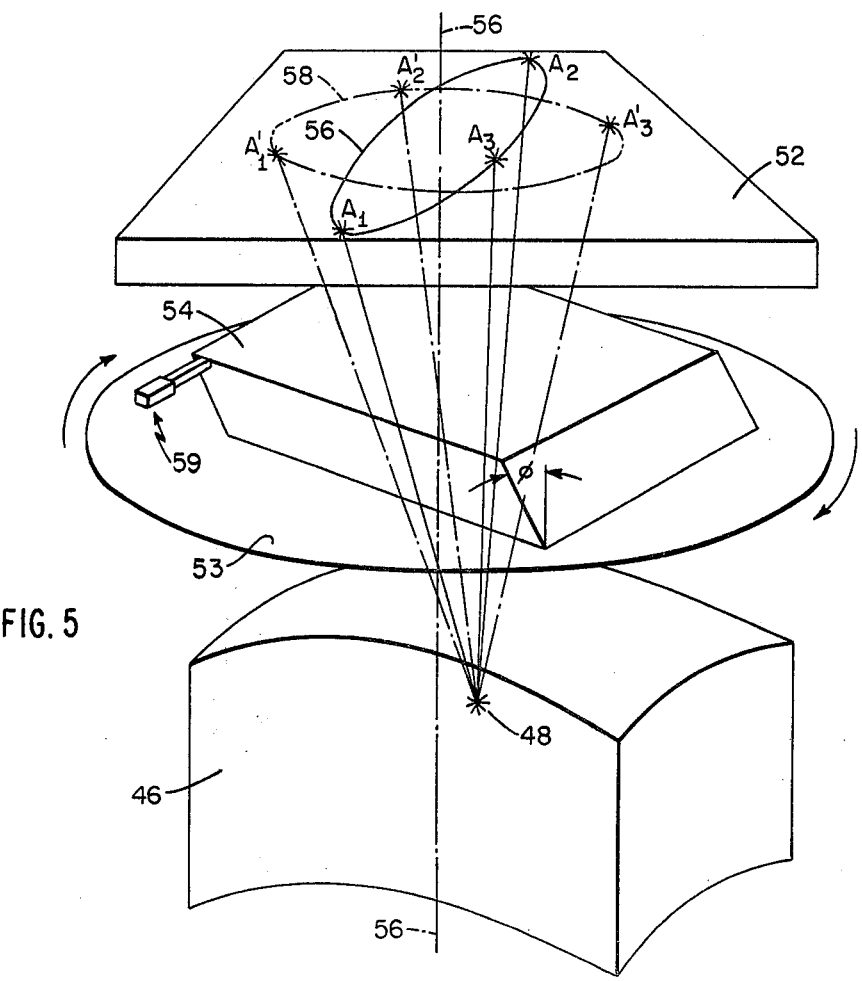
FIG. 5 shows a functional view of the collimator of the present invention in a tomographic application.

With respect to FIG. 5 an application of the invention in tomography is illustrated. As shown there an object 46 under study contains a region 48 of interest which is a localized source of radiation. Detectors 52 are provided to receive radiation from the object 46 through a collimator stack 54 in accordance with the present invention. The collimator stack 54 is rotatable on a support 53, about an axis 56 in a known manner according to conventional tomography practice. During the rotation of this collimator stack, the angle of skew $\phi$ may be varied so that the radiation path projected from the source 48 will describe an elliptical or other desired path 56 through points A1, A2 and A3 at the detectors 52 due to the changing acceptance axis of the collimator stack 54. Furthermore, this pattern may be changed during an exposure session to track one or more different paths such as path 58 through points A′1, A′2 and A′3. While the computer analysis techniques of tomography will still permit the generation of the desired tomographic image, the distribution of the sensed radioactivity throughout a large variety of view angles will improve image contrast within the final tomogram.

The variation in skew angle to produce the different paths 56 and 58 is continuous during the rotation of stack 54. To produce the elliptical pattern, other forms of continuous, or step variations in skew angle can be produced as desired. For this purpose a mechanism 59 mounted between stack 54 and support 53 may be used.

Figure 6A:
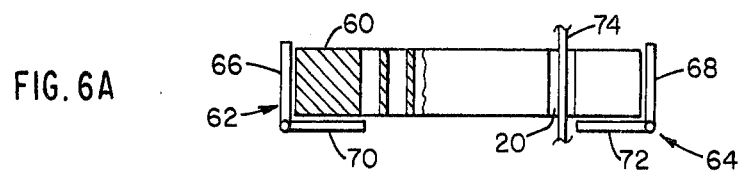
FIG. 6A shows a cross sectional view of a collimator and mechanism for adjusting angle of view.
Figure 6B:
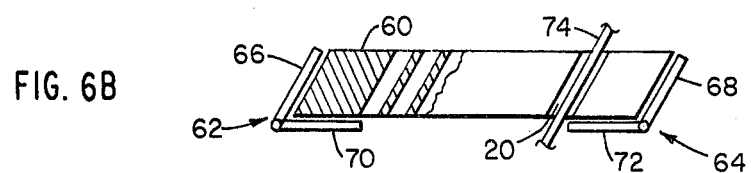
FIG. 6B shows the collimator of FIG. 6A at a non perpendicular angle of view.

A mechanism for providing controlled skewing of the collimator stack in accordance with the present invention is illustrated with respect to FIGS. 6A and 6B. As shown there, a collimator stack 60 is held in alignment by an opposing pair of hinged mounts 62 and 64, the upper arm portions 66 and 68 of which are pivoted with respect to a bottom support plate 70 and 72 respectively. By angling the upper arm portions 66 and 68 with respect to the bottom plates 70 and 72 the entire collimator stack 60 can be skewed to a desired angle of view by sliding each of the plates within the stack 60 relative to each other. In order to help maintain a parallel alignment of the apertures in the plates, knife edge guides 74 may be provided to fit within the grooves or notches 20. In this manner the parallel relationship of the channels through the plate apertures may be maintained as the stack is skewed. Clamping means of conventional design may be used to hold the stack together.

It is also possible, using the photo-etch technique typically employed to produce the apertured pattern of each plate, to alter the alignment of apertures from plate to plate by slightly adjusting the magnification in the photo exposure of the etched pattern from plate to plate. In this manner a collimator stack having a converging (or, in the opposite direction, diverging) character can be accurately produced. Such a collimator stack can also be adjusted in angle of view, and thus point of convergence, in the manner discussed above with respect to FIGS. 6A and 6B.

Figure 7:
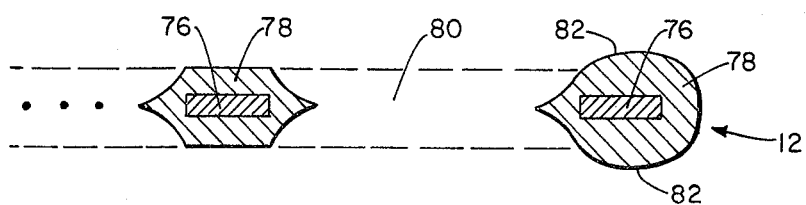
FIG. 7 is a cross sectional view of a plate of the present collimator showing an alternative fabrication.

As noted above, the use of tungsten for the material of the plates 12 is convenient in that it provides a high degree of radiation absorption as well as ease of photo production. It is also possible to provide a support grid for the plate as a stainless steel stamping 76 (FIG. 7). In this case it is preferable to imbed the stainless steel in a lead or lead tin alloy coating 78. The lead coating may be etched to provide control over the pattern of apertures 80 through each plate. Additionally, a leaded plastic may be used and appropriately apertured. It is also possible to provide, around the periphery of each plate, a slightly greater thickness as shown in the peripheral region 82, so that the plates are supported entirely at their periphery. This prevents the scaling of the lead in the region of apertures 80. The stainless steel support mesh 76 provides sufficient tensile strength, while the lead coating stiffens the members in compression so as to support the plates in their center and to transmit the skewing forces without buckling.

As further modifications or improvements to the plate design illustrated with respect to FIG. 7, the lead coating 78 may be itself further coated with a stainless steel or plastic layer in order to further reduce sliding friction when rubbing against the surface of adjoining plates. Additionally, the apertures 80 may be filled with a low radiation-absorbing plastic such as a hardened foam in order to further improve the structural and sliding qualities of the collimator plates.

The above description is intended as exemplary only, the scope of the invention to be determined solely by reference to the following claims.

What is claimed is:

1. A radiation collimator comprising:
   a plurality of sheets of a generally radiation absorbing material, said sheets being apertured in a predetermined two dimensional pattern over a substantial area of said sheets; and
   means for stacking said sheets with said apertures in alignment to provide a set of radiation channels through the stack of sheets with a predetermined orientation and to provide for angular variation in said predetermined orientation by skewing of said sheets within said stack;
   said set of radiation channels forming a collimated view through said sheets defined by said predetermined orientation;
   the pattern of apertures in each sheet being selected relative to the pattern of apertures in adjacent sheets of said stack to provide said predetermined orientation to the set of radiation channels with a characteristic within the range of characteristics from divergence to convergence.

2. The collimator of claim 1 wherein said sheets are fabricated of tungsten.

3. The collimator of claim 1 or 2 wherein said sheets have a thickness of approximately 0.25 mm.

4. The collimator of claim 1 wherein said sheets include a lead coating.

5. The collimator of claim 4 wherein said sheets include a stainless steel support mesh for said lead coating.

6. The collimator of claim 1 wherein each of said sheets in said stack of sheets includes a peripheral portion of increased thickness whereby said sheets as stacked are supported with their central portions physically separated from each other.

7. The collimator of claim 1 wherein said sheets include a peripheral notch with the sheets as stacked having said notches in predetermined alignment.

8. The collimator of claim 7 further including means for engaging said notches in the sheets as stacked to provide registration and alignment control.

9. The collimator of claim 1 wherein said apertures are approximately 2 mm square.

10. The collimator of claim 1 wherein said stacking means is adapted for holding a variable number of said sheets in the stack of sheets.

11. The collimator of claim 1 wherein each said sheet comprises stainless steel having a plating thereon of a higher radiation absorbing material.

12. The collimator of claim 11 wherein said plating is a lead tin alloy.

13. The collimator of claim 1 wherein said apertures are filled with a low radiation absorbing material.

14. A method for making radiation exposures of a subject under study through a collimator consisting of a set of sheets apertured in a two dimensional pattern and stacked with the apertures in alignment to provide a set of radiation channels through the stack with a predetermined orientation to the collimation thereby produced, the method comprising the steps of:
   rotating said collimator about a desired tomographic viewing axis of a subject under study;
   varying said predetermined orientation by skewing the stack of sheets during the rotation of said collimator;
   the pattern of apertures in each sheet being selected relative to the pattern of apertures in adjacent sheets of said stack to provide said predetermined orientation to the set of radiation channels with a characteristic within the range of characteristics from divergence to convergence.

15. The method of claim 14 wherein said varying step includes continuous variations of orientation.

16. The method of claim 14 wherein said varying step includes step variations of orientation.

* * * * *